United States Patent [19]

Lymneos

[11] Patent Number: 4,501,969
[45] Date of Patent: Feb. 26, 1985

[54] PHOTOMETRIC APPARATUS AND PROCESS

[75] Inventor: Anthony C. Lymneos, West Upton, Mass.

[73] Assignee: Millipore Corporation, Bedford, Mass.

[21] Appl. No.: 356,064

[22] Filed: Mar. 8, 1982

[51] Int. Cl.³ .............................................. G01J 5/08
[52] U.S. Cl. .................................................. 250/373
[58] Field of Search ........................................ 250/373

[56] References Cited

U.S. PATENT DOCUMENTS

| | | | |
|---|---|---|---|
| 3,674,373 | 7/1972 | Waters et al. | 356/130 |
| 3,792,929 | 2/1974 | Alpert | 356/427 |
| 4,011,451 | 3/1977 | Nelson | 250/343 |
| 4,276,475 | 6/1981 | Nelson | 250/373 |

Primary Examiner—Bruce C. Anderson
Assistant Examiner—Constantine Hannaher
Attorney, Agent, or Firm—Andrew T. Karnakis; Paul J. Cook

[57] ABSTRACT

Novel photometric apparatus advantageously having a conical shaped flow-cell comprising a light source proximate the narrow end and a photosensitive detector at the wider end of the cell. The flow-cell adequately compensates for a lens effect that has been discovered to be a substantial factor in electro-magnetic energy absorption studies on liquid streams. A light beam from the light source is passed through an elliptical aperture to render the beam substantially circular prior to entering the flow-cell.

22 Claims, 3 Drawing Figures

PHOTOMETRIC APPARATUS AND PROCESS

BACKGROUND OF THE INVENTION

This invention relates to a method and apparatus for measuring the light absorbance by a fluid. In analysis of very small quantities of liquids, it has been recognized that the physical conditioning of the fluid must be done very carefully. Thus, for example, in the field of liquid chromatography wherein very small, continuously-flowing streams of liquid are measured, care is taken to minimize mechanical and thermal disturbance of the liquid stream between the chromatographic column and analytical apparatus in which the liquid stream from the column is to be continuously analyzed. The primary objective is to present, to a transparent sample cell, the precise sequence of changing liquid composition that leaves the chromatography column.

The rationale and particulars of such apparatus are described in the art. For example, see U.S. Pat. No. 3,674,373 to Waters, Hutchins and Abrahams which involves a refractometer particularly well adapted to receive such a liquid stream. In general, the approach is to minimize the conduit path through which the liquid to be analyzed must travel and to provide a maximum thermal-conditioning of the liquid within such a minimized path. This generally illustrates the art-recognized importance of careful handling of sample liquid between its point of origin and the sample cell in which it is to be subjected to analysis, usually analysis which measures an effect of the sample liquid stream on some radiation directed into a flow-cell through which the stream passes.

Investigators have also realized that some attention must be given to the physical condition of the fluid even after it enters the flow-cell. Consequently, flow-cells have been made ever smaller to avoid mixing and peak-spreading effects and, in some cases, a positive thermal equilibration of the cell with the liquid has been sought in order to avoid light-shimmering effects along the cell walls. Moreover, the cells are usually positioned with outlets so placed that any entrained gas bubbles tend to be carried upwardly out of the cell.

U.S. Pat. No. 3,792,929, to Alpert, it has been noted, seems to disclose a conical sample-holding cell. The patent is related to static-sample devices and in no way involves fluid lenses of any type. The apparent and relative dimensions of the Alpert cell would not allow its effective use in most continuous-flow monitoring systems such as are encountered in liquid chromatographic work and the like.

U.S. Pat. No. 4,011,451 to Nelson discloses a photometer utilizing a generally conical sample cell with the smaller end of the cell being nearer the light source. The photometer substantially eliminates spurious radiation signals generated by a lens type effect caused by liquids of different refractive index that leads to undesirable light absorbance by the sample cell walls. The apparatus described in U.S. Pat. No. 4,011,451 utilizes a primary light source having a wavelength of 253.7 nanometers.

Presently there is a need for photometric apparatus which utilizes a shorter ultraviolet light wavelength than that utilized by prior art photometric apparatus to permit detection of a wide variety of biological compounds. A suitable shorter primary light source has a wavelength of 214 nanometers produced from a zinc lamp or a wavelength of 229 nanometers from a cadmium lamp. However, the shorter wavelength light has lower energy than the 253.7 nanometer light utilized in presently available photometric apparatus. This causes a higher noise to signal ratio which leads to errors in measurement. Furthermore, it would be desirable to provide a photometric process and apparatus which permits utilizing short wavelength ultraviolet light.

SUMMARY OF THE INVENTION

This invention is particularly useful in a photometric apparatus which utilizes a reference cell in conjuction with a sample cell wherein a portion of a common light source is passed through the sample cell and reference cell simultaneously. It has been found that the optics utilized to split the common light source into two columnated light beams which are then directed through the reference cell and the sample cell each being offset from the central optical axis causes each columnated light beam to have an elliptical cross-section. When utilizing short wavelength light, light energy entering each cell is lost thereby undesirably increasing the noise to signal ratio. In accordance with this invention, an elliptical aperture is interposed between (a) the light source and lens assembly that forms two light beams and (b) the lens assembly that directs the light beams into the reference cell and sample cell. The elliptical aperture has its major axis orthogonal to the major axis of the elliptical light beam formed with a circular aperture. The major axis of the elliptical aperture also is parallel to a line joining the center lines of the sample cell and the reference cell.

DESCRIPTION OF SPECIFIC EMBODIMENTS

Figure 1:
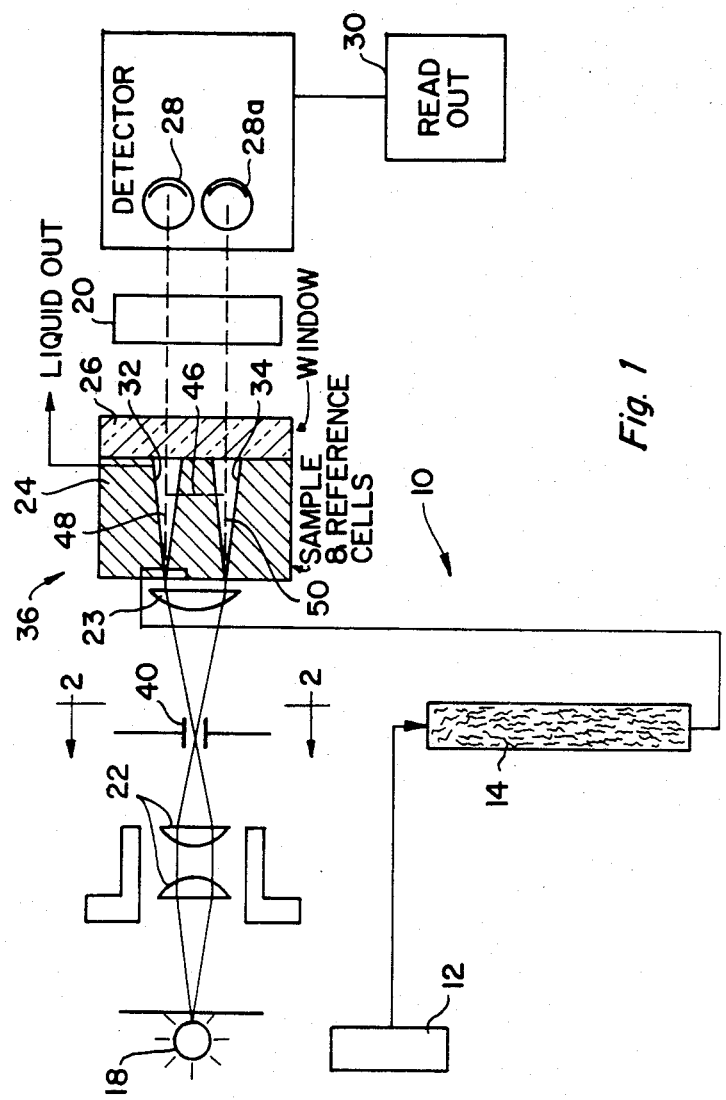
FIG. 1 is a schematic diagram of an analytical apparatus of this invention.

The invention is particularly useful in photometric apparatus utilizing a tapered sample cell and reference cell.

Substantial spurious radiation signals are generated by differences in refractive indices and particularly by a lens-type effect caused by liquids of different refractive index and especially laminar-flow patterns at the interface of compositions differing in refractive index; the effect is troublesome in small cylindrical photometer sample-cells. These laminar flow patterns will sometimes be called "dynamic liquid lenses" in this description. In general the worst problems have been encountered in flow-cells in the microliter range, say flow-cells having a diameter of less than about 2 millimeters. In the usual situation the flow path of an ultraviolet absorptometer cell is selected to be 1 centimeter in length, and a flow cell of 2 millimeters maximum diameter will have a volume of less than about 32 microliters. As the diameter increases the lens effect caused by a given rate of laminar-flow tends to decrease; but a mere increase in diameter of a cylindrical flow path to avoid the lens effect is not practical because the increased diameter would result in either (1) a large increase in the volume of the tube or (2) a substantial decrease in length of the tube. A large increase in volume is untenable because the ability of the apparatus to detect very small samples would be substantially limited by dilution facts. The length of the cell cannot be markedly reduced without proportionately decreasing the magnitude of light absorbed by a given solution flowing through a cell. Still other conceivable tube configurations would give disadvantageous liquid flow patterns.

Because the problem of these dynamic fluid lenses is primarily encountered at the point of changing compositions, its solution has been found to enhance both the quantitative and qualitative analytical capabilities of liquid chromatographic systems and like analytical systems where constantly changing compositions are inherent in the method. However, the apparatus is useful in other lens-inducing situations encountered in the process industry; e.g., where the dynamic fluid lens may be induced by temperature change or other phenomena that result in formation of a refractive index gradient within the flow-cell.

The wall of the flow-cell advantageously forms a diverging surface of rotation whereby the walls form an angle of divergence of at least about one angular degree with the axis of the cell. An optical system is advantageously provided which avoids any substantial radiation from entering the cell at sharp angles which would result in the radiation to impinge on the walls of the cells. An angle of about 1.5 degrees or slightly greater provides sufficient widening to substantially dissipate the undesirable effect of the dynamic liquid lens formed at the interface of water and most organic solvents. The improvement is largely achieved by collecting refracted light, which would have otherwise been absorbed on the wall of the cell, but it is also believed the reduction in velocity of the stream during its transit through the cell—usually a reduction of over 50 percent—causes a dissipation of the lens effect itself which reduces the amount of refracted light directed against the walls of the cell. Angles of divergence between the axis of the flowpath and the wall of the cell of 1° to 3° are most advantageous; larger angles only become problems because they usually dictate a larger cell size.

In liquid chromatographic applications, best results will be achieved if the apparatus to be used with the flow-cell is selected to achieve the most ideal flow pattern possible, i.e., the flow pattern most nearly achieving plug flow. This is true of all flow in a liquid chromatographic system: flow from sample injection to the column and flow between the column and the analytical component of the system. Such apparatus is available: an injector advantageously used is that available under the trade description Model U6K Injector by Waters Associates, Inc. A pumping system, advantageously used to feed liquid into a high pressure column, is that available from the same source under the trade designation Model 6000 Solvent Delivery System. However, as will be obvious to those skilled in the art, other such apparatus will be generally useful in many applications in which the instant invention is advantageously used.

A typical elliptical aperture utilized in the present invention generally has a major axis of about 1.52 mm (0.06 inch) and a minor axis of about 1.02 mm (0.04 inch) and is positioned about 13.72 mm (0.54 inch) from the circular entrances to the sample cell and reference cell which have a diameter of about 1.04 mm (0.041 inch). It is to be understood that the actual dimensions of the ellipse is dependent upon the sizes of the cell openings, the distance of the cells from the central optical axis and the size of the lens adjacent the cell entrances.

It will also be obvious to those skilled in the art that a number of modifications can be made in the shape of the wall structure of the flow-cell. For example, further enlargement of the cell conduit over that defined minimal conical shape will yield an operable cell that will avoid the effect of the dynamic liquid lens but will also be larger in size and therefore less favorable for many applications. Such enlargement is nonfunctional with respect to the present invention. However other such shapes including such as catenoidal horns, hyperbolic horns, parabolic and hyperbolic surfaces as well as similar surfaces of revolution are all intended to be covered by the term "generally truncated cone" as used in this application. Such shapes may on some occasions be favorable in view of effects caused by special flow properties of the fluid components which form the dynamic lens, temperature profiles across the cell, friction effects along the surface of the wall or the like. "Generally conical", therefore, is meant to include any flow-cell wherein the inlet port is smaller than the outlet port and the cross-section of the cell is progressively larger as measured closer to the outlet port.

It is to be realized that the larger end of the cone must be toward the detector. It is possible, however, to reverse the direction of flow of the liquid to be analyzed through the cell. Best practice is to avoid this situation or, if for some reason it is desirable, to arrange the attitude of the cell so that any minute gas bubbles can be displaced upwardly toward the outlet port of the cell.

In chromatographic related analytical operations and other such operations which monitor microliter quantities of a flowing sample, the length-to-average diameter ratio of the flow cell is advantageously at least 5 to 1. It is primarily the monitoring of such small samples, rather than inherent optical considerations, which make angles of divergence greater than 3° undesirable for many applications.

One additional advantage of the apparatus disclosed herein is that fact that, for some applications, it allows the light source to be brought (physically, or by optical means) closer to the sample cell without undue losses of light by refraction and light scattering occurring primarily at the interfaces of gas-lens and liquid-lens interfaces.

Although, the above invention has been described largely in terms of flow cells, it should be recognized that it also has advantage in non-flow cell situations wherein liquids of substantial difference in refractive index are used with the same optical system.

It is also to be understood that while this invention is particularly useful in conjunction with short wavelength light sources, it also is useful with longer wavelength light sources such as 253.7 nanometers since the optics utilized therein also cause the light beam entering the sample cell and reference cell to become elliptical, but to a lesser degree.

FIG. 1 illustrates an analytical system 10 comprising a source 12 of a liquid to be analyzed, a liquid chromatography column 14, a light source 18, an interference filter 20, elliptical aperture 40, a lens system 22, front lens 23, main housing wall of sample cell 24, a rear window 26 and photoelectric detector 28. Signals from photo detector 28 and a reference detector 28a are processed according to known techniques to provide a suitable electronic signal which may be used as a control means or as is more frequent, to provide a visible recording on a recorder means 30.

An important feature in FIG. 1 is the sample cell 24 which incorporates the conical flowpath 32. However, this innovation directly enhances the performance of the entire system by providing means to take the liquid output from chromatographic column 14 and process it in the ultraviolet absorption apparatus so that the resulting light reaching detector 28 is substantially free of detrimental loss of light due to the influence of dynamic liquid lenses.

In the apparatus of FIG. 1, the light source is rated at 2.4 watts and has principal wavelength of 214 nanometers. The volume of the sample cell is about 12.5 microliters: it is about 1.02 mm (0.04 inches) in diameter at the inlet end, about 1.78 mm (0.07 inches) in diameter at the outlet end and about 9.47 mm (0.373 inches) in length. A reference flow-cell 34 is positioned within cell assembly 36, as is common in the photometric analysis of liquids. This cell may be empty, full of a stagnant liquid or having a flowing reference fluid therein.

Figure 2:
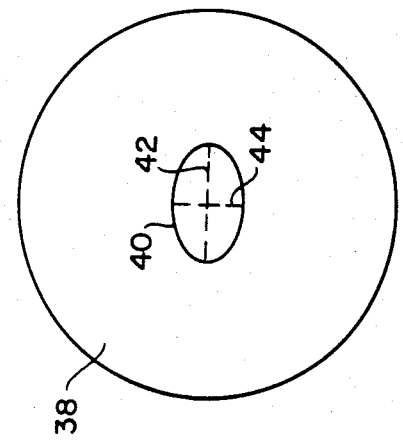
FIG. 2 is a view of the oval aperture taken along line 2—2 of FIG. 1.

Referring to FIG. 2, high shield 38 includes an elliptical aperture 40 having a major axis 42 and a minor axis 44. The major axis 42 is parallel to a line 46 joining and perpendicular to the center lines 48 and 50 of sample cell 32 and reference cell 34.

Figure 3:
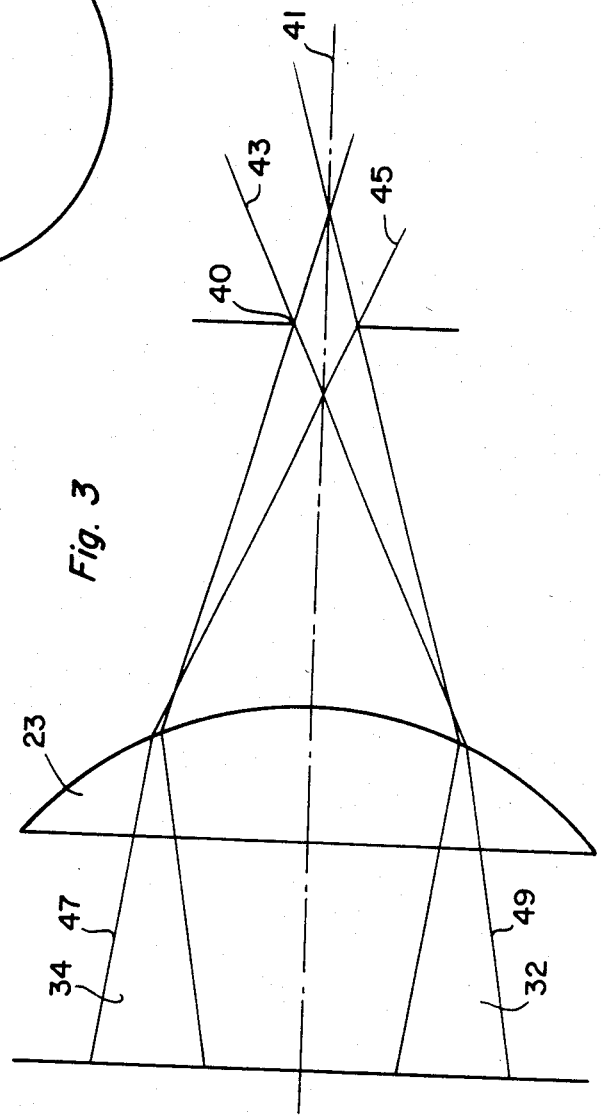
FIG. 3 is a schematic view of the optics of this invention.

Referring to FIG. 3 the elliptical aperture 40 is positioned a distance from cells 32 and 34 along the central optical axis at the point where the distance between light ray 43 and the central optical axis 41 equals the distance between light ray 45 and central optical axis 41. Light ray 43 follows surface 49 of cell 32 and light ray 45 follows surface 47 of cell 34.

What is claimed is:

1. In a photometer of the type utilizing a light source, a sample cell adapted to transmit a continuously-flowing liquid to be analyzed from an inlet port near one end thereof through a flowpath to an outlet port near the other end thereof, a means for measuring the absorption of light in said sample cell, a light detector forming means to receive substantially all nonabsorbed light transmitted from said sample cell, means for eliminating liquid lens effects, said means comprising a generally conical sample cell, a smaller end of said sample cell being nearer said light source, such that there is substantially reduced loss of light refracted by said lenses on walls of said sample cell, wherein improvement comprises an elliptical aperture interposed between said light source and said sample cell to render a light beam entering said sample cell substantially circular.

2. A photometer as defined in claim 1 wherein said light source and said measuring means are so selected that said photometer is an ultraviolet absorbance detector.

3. A photometer as defined in claim 2 wherein an angle of divergence between an axis of said flowpath and the wall of said flow-cell is from 1° to 3°.

4. A photometer as defined in claim 2 wherein said sample cell has a volume of less than 32 microliters and a maximum diameter of less than 2 millimeters.

5. A photometer as defined in claim 4 wherein an angle of divergence between an axis of said flowpath and the wall of said flow-cell is from 1° to 3°.

6. A photometer as defined in claim 1 wherein said sample cell has a volume of less than 32 microliters and a maximum diameter of less than 2 millimeters.

7. A photometer as defined in claim 6 wherin an angle of divergence between an axis of said flowpath and the wall of said flow-cell is from 1° to 3°.

8. A photometer as defined in claim 1 wherein an angle of divergence between an axis of said flowpath and the wall of said flow-cell is from 1° to 3°.

9. A photometer as defined in claim 8 wherein the length-to-average diameter ratio of the flowpath is at least 5:1.

10. In a process for measuring the radiation absorptivity of a flowing liquid sample which comprises a plurality of sequential liquid compositions in a laminar flow mode, substantially eliminating the interference of dynamic liquid lens effects with said measuring by
   a. feeding said liquid into a generally conical sample cell proximate a smaller cross-sectional end thereof;
   b. removing said liquid from said sample cell at a larger cross-sectional end thereof,
   c. measuring the radiation absorptivity of said liquid through said cell, said measurement being carried out by detection at said larger end of said cell, substantially all of the nonabsorbed radiation from a source proximate the smaller end of said cell, and the improvement comprising rendering a light beam or entering said sample cell containing said sample by
   d. passing the light beam through an elliptical aperture prior to passing said light beam into said sample cell.

11. A process as defined in claim 10 wherein the radiation being measured is ultraviolet light.

12. A process as defined in claim 11 wherein the velocity of the sample liquid is decreased by at least about 50 percent during its movement from the inlet end of said sample cell to the outlet end of said cell.

13. A process as defined in claim 10 wherein the volume of liquid sample in said flow cell is maintained at less than about 32 microliters and wherein said maximum diameter of said cell is 2 millimeters.

14. A process as defined in claim 13 wherein the velocity of the sample liquid is decreased by at least about 50 percent during its movement from the inlet end of said sample cell to the outlet end of said cell.

15. A process as defined in claim 10 wherein the velocity of the sample liquid is decreased by at least about 50 percent during its movement from the inlet end of said sample cell to the outlet end of said cell.

16. In a liquid chromatographic analytical apparatus of the type having a liquid chromatographic column adapted to emit a liquid stream comprising a series of sequentially-arranged liquid compositions, and means for conducting said stream to a photometer of the type comprising a sample flow-cell forming a conduit for said liquid stream, a means to provide a source of radiation, and a radiation detector arranged with respect to said conduit to form a radiation path therethrough, wherein said radiation detector forms means to receive substantially all nonabsorbed light transmitted through said sample cell, and including means for eliminating the distortion of said radiation by dynamic liquid lens effects comprising a flow-cell which forms a truncated, generally conical, flowpath, a smaller end of said cone being nearer said radiation means such that there is no substantial loss of refracted radiation on the walls of said flow-cell, wherein the improvement comprises that the light beam is passed through an elliptical aperture prior to entering said sample cell.

17. A chromatographic apparatus as defined in claim 16 wherein said light source and said detecting means are so selected that said radiation detector is an ultraviolet radiation detector.

18. A chromatographic apparatus as defined in claim 17 wherein said flow-cell has a maximum diameter of 2 millimeters.

19. A chromatograpic apparatus as defined in claim 18 wherein the angle of divergence between the conical wall and an axis of said flowpath is from 1° to 3 .

20. A chromatographic apparatus as defined in claim 19 wherein said flowpath has a length-to-average diameter ratio of at least 5:1.

21. A chromatographic apparatus as defined in claim 16 wherein said flow-cell has a maximum diameter of 2 millimeters.

22. A chromatographic apparatus as defined in claim 16 wherein the angle of divergence between the conical wall and an axis of said flowpath is from 1° to 3°.

* * * * *